United States Patent
Novak et al.

(10) Patent No.: US 7,950,271 B2
(45) Date of Patent: May 31, 2011

(54) GATED BETA-MOLYBDENUM OXIDE SENSOR

(75) Inventors: James Novak, Austin, TX (US); Prabhu Soundarrajan, Valencia, CA (US)

(73) Assignee: Applied Nanotech Holdings, Inc., Austin, TX (US)

( * ) Notice: Subject to any disclaimer, the term of this patent is extended or adjusted under 35 U.S.C. 154(b) by 255 days.

(21) Appl. No.: 12/103,628

(22) Filed: Apr. 15, 2008

(65) Prior Publication Data
US 2009/0256215 A1  Oct. 15, 2009

Related U.S. Application Data

(63) Continuation-in-part of application No. 11/375,791, filed on Mar. 15, 2006, now abandoned.

(60) Provisional application No. 60/663,286, filed on Mar. 18, 2005.

(51) Int. Cl.
*G01N 7/00* (2006.01)
(52) U.S. Cl. .......... 73/31.06; 257/253; 977/957
(58) Field of Classification Search .......... 257/253, 257/414, 431, E23.003; 422/83, 385; 73/25.03, 73/31.05, 31.06; 977/953–957; 204/400; 205/785.5
See application file for complete search history.

(56) References Cited

U.S. PATENT DOCUMENTS

| | | | |
|---|---|---|---|
| 6,173,602 B1 * | 1/2001 | Moseley | 73/31.06 |
| 2003/0059342 A1 | 3/2003 | Elkind | |
| 2003/0217586 A1 * | 11/2003 | Gouma | 73/31.06 |
| 2006/0277974 A1 * | 12/2006 | Gouma et al. | 73/25.03 |

OTHER PUBLICATIONS

Doll, Theodor; Advanced Gas Sensing: The Electroadsorptive Effect and Related Techniques. Kluwer Academic Publishers: In re Chapter 4: Wollenstein et al., Advanced Gas Sensing, 2003, p. 85-99.*

Zhenan Tang et al., "An integrated gas sensor based on tin oxide thin-film and improved micro-hotplate," Sensors and Actuators, B 46 (1998) pp. 174-179.

Hisahito Ogawa et al., "Electrical Properties of Tin Oxide Ultrafine Particle Films," J. Electrochem. Soc.: Solid-State Science and Technology, vol. 128, No. 9, Sep. 1981, pp. 2020-2025.

M. Scheinert et al., "Electrically Controlled Metal Oxide Gas Sensor Designed with PROSA-CHEM," Proceedings of IEEE Sensors 2002, Jul. 11, 2002, pp. 356-360.

J. Wollenstein et al., "New Materials and Technologies for Micromachined Metal Oxide Gas Sensor Arrays," Proceedings of IEEE Sensors 2002, Jul. 11, 2002, pp. 404-408.

R.E. Presley et al., "Tin Oxide Transparent Thin-Film Transistors," J. Phys. D: Appl. Phys. 37 (2004) 2810-2813.

J. Wollenstein et al., "A Gas Sensitive Tin Oxide Thin-Film Transistor," Advanced Gas Sensing (2003), pp. 85-99.

(Continued)

*Primary Examiner* — N Drew Richards
*Assistant Examiner* — John P Dulka
(74) *Attorney, Agent, or Firm* — Kelly Kordzik; Matheson Keys Garsson & Kordzik PLLC

(57) ABSTRACT

An apparatus for sensing an analyte gas is provided. The apparatus may include a signal amplifier that may include a thin film transistor that may include a semiconducting film that may include a metal oxide capable of chemical interaction with the analyte gas, such as carbon monoxide. The apparatus may be tuned for detecting the analyte gas by varying the gate voltage of the transistor.

18 Claims, 8 Drawing Sheets

OTHER PUBLICATIONS

Applied Nanotechnologies Introduces Carbon Monoxide Sensor; Azonano.com; Posted 17th Feb. 2006; www.azonano.com (discusses material from Nano-Proprietary, Inc.'s website: http://www.nano-proprietary.com).

Gutierrez-Osuna, R.; Machine Olfaction: Advanced Excitation Methods for Inorganic Chemoresistors; Power Point presentation from Wright State University; pp. 1-27.

Korotchenkov, Ghennady et al.; $SnO_2$ Thin Film Gas Sensors for Fire-Alarm Systems; *Elsevier*; Sensors and Actuators B 54 (1999) 191-196.

Yu, Choongho et al.; Integration of Metal Oxide Nanobelts with Microsystems for Nerve Agent Detection; *Applied Physics Letters*, 86, 063101 (2005) (Downloaded Feb. 5, 2005 to 130.207.165.29. Copyright, see http://apl.aip.org/apl/copyright.jsp.

Anderson, Teresa; All Aboard; Reference: http://www.securitymanagement.com/library/001024.html.

Eranna, G., et al; Oxide Materials for Development of Integrated Gas Sensors—A Comprehensive Review / Integrated Gas Sensors—A Comprehensive Review; *Critical Reviews in Solid State and Materials Sciences*; 29: pp. 111-188, 2004; (Additional page range note in upper left hand corner: pp. 1-78).

Barsan, N. et al.; Understanding the Fundamental Principles of Metal Oxide Based Gas Sensors; The Example of CO Sensing with $SnO_2$ Sensors in the Presence of Humidity (Topical Review); *Journal of Physics: Condensed Matter*; vol. 15 (2003) pp. R813-R839.

Tomchenko, Alexey A. et al.; Detection of Chemical Warfare Agents Using Nanostructured Metal Oxide Sensors; *Elsevier; Sensors and Actuators* B 108 (2005) 41-55.

Neri, Giovanni et al; A Highly Sensitive Oxygen Sensor Operating at Room Temperature Based on Platinum-Doped $In_2O_3$ Nanocrystals; *Chem. Commun.*, Nov. 8, 2005; 6032-6034. Copyright—The Royal Society of Chemistry; 2005.

Fan, Zhiyong et al.; ZnO Nanowire Field-Effect Transistor and Oxygen Sensing Property; *Applied Physics Letters*; vol. 85, No. 24, Dec. 13, 2004, pp. 5923-5925.

Dalin, Johan; Fabrication and Characterisation of a Novel MOSFET Gas Sensor; Final Thesis at Linkopings Institute of Technology Performed at Fraunhofer Institute for Physical Measurement Techniques; pp. I-XII and 1-82.

Liu, H. et al; Size-Selective Electrodeposition of Meso-Scale Metal Particles: A General Method; *Electrochimica Acta*; vol. 47 (2001), pp. 671-677.

Comini, E. et al.; Carbon Monoxide Response of Molybdenum Oxide Thin Films Deposited by Different Techniques; *Elsevier; Sensors and Actuators*; B 68 (2000) 168-174.

Vincent et al.; Structural Aspects of Molybdenum Bronzes and Molybdenum Oxides in Relation to Their Low-Dimensional Transport Properties; *Physics and Chemistry Materials with Low-Dimensional Structures*; vol. 11 (1989) 49-85.

McCarron III, E.M.; β-$MoO_3$: a Metastable Analogue of $WO_3$; *J. Chem. Soc., Chem. Commun.*, (1986) 336-338.

Spevack, et al.; Thermal Reduction of $MoO_3$; *J. Phys. Chem.*; vol. 96 (1992) 9029-9035.

Ming et al.: Large-Scale Organizations of $MoO_3$ Nanoplatelets with Single-Crystalline $MoO_3(4,4'\text{-bipyridyl})_{0.5}$; *J. Phys. Chem. B.*; vol. 107, No. 12; (Mar. 27, 2003) 2619-2622.

McEvoy et al.; Electrochemical Preparation of Molybdenum Trioxide Thin Films: Effect of Sintering on Electrochromic and Electroinsertion Properites; *Langmuir*; vol. 19 (2003) 4316-4326.

McEvoy et al.: Spatially Resolved Imaging of Inhomogeneous Charge Transfer Behavior in Polymorphous Molybdenum Oxide; *Langmuir*; vol. 21 (2005) 3521-3528.

Ramirez et al.: Synthesis of β-$MoO_3$ by Vacuum Drying and its Structural and Electrochemical Characterisation; *Materials Letters*; vol. 57 (2003) 1034-1039.

Dieterle et al.; Raman Spectroscopy of Molybdenum Oxides; *Phys. Chem. Chem. Phys.*, vol. 4, (2002) 812-821.

\* cited by examiner

GATED BETA-MOLYBDENUM OXIDE SENSOR

CROSS-REFERENCE TO RELATED APPLICATIONS

The present application is a Continuation-in-Part of and claims priority to U.S. patent application Ser. No. 11/375,791, filed Mar. 15, 2006 now abandoned which claims priority to U.S. Provisional Patent Application Ser. No. 60/663,286, filed Mar. 18, 2005, entitled "Nanoparticle Metal Oxide Thin-Film Transistor for Carbon Monoxide Detection," both of which are hereby incorporated herein by reference.

STATEMENT REGARDING FEDERALLY SPONSORED RESEARCH OR DEVELOPMENT

The United States has certain rights in this invention pursuant to Grant No. FA8650-05-M-6562 awarded by the Air Force.

TECHNICAL FIELD

The present invention relates in general to gas sensors. More particularly the present invention relates to gas sensors that operate by applying a gate voltage so as to tune detection of a current through a layer of a compound that is capable of chemical interaction with an analyte gas. Additionally, other methods could be used to tune the detection of an analyte, including, optical excitation, chemical dopants, surface chemical layers and combinations thereof. Additionally, the application of an external force, such as a gate bias, helps to eliminate or greatly reduce the requirement for a heated substrate surface. Still more particularly, the present invention relates to thin film gated metal oxide detectors adapted for detection of analyte gases, such a carbon monoxide.

BACKGROUND INFORMATION

Heated Metal Oxide Sensors

There is a large background of information regarding metal oxide chemical sensors. These have all been on heated substrates or measured by electrochemical detection. For example see Eranna, G. et al. "Oxide Materials for Development of Integrated Gas Sensors—A Comprehensive Review" *Critical Reviews in Solids State and Materials Sciences,* 29: 111-188, 2004 (herein denoted in Ref. 1) and the references therein.

It is desirable to provide sensors for detecting ambient levels of gases, particularly noxious gases. Heated metal oxide sensors are well studied in the literature. As a recent review, Eranna et al, (table 23, page 174) shows the range of gases that can be detected and the metal oxides that are sensitive to each gas.

Many metal oxides are semiconducting. This means there is an energy gap between the population of electrons called the valance band and the conduction band where these electrons can move through the material. This energy gap is commonly called the band gap and denoted as $E_g$. The metal oxide sensors take advantage of this semiconducting nature by promoting electrons from the valence band to the conduction band through heat. This thermal excitation of electrons can change the surface energy of the metal oxide promoting facile chemical reactions.

Metal oxides typically have an amorphous crystal structure. This means there will be individual crystalline grains but that there is no long-range order to the surface. The interface between each crystallite creates a grain boundary. Conduction through a metal oxide is limited by the energy barrier created at each grain boundary. In addition to the change in surface energy heat changes the energy level of barriers created at these individual grain boundaries.

Carbon monoxide poisoning presents a major problem in civilian and military sectors. It is estimated that more than 500 people accidentally die from carbon monoxide ("CO") poisoning each year in the United States, more than from any other poison. In addition, an estimated 10,000 people are treated annually for symptoms of CO exposure. While most of the household CO related incidents could be identified and treated, the situation is more critical in aircraft environments where a lack of suitable monitoring devices is available.

Carbon monoxide has about 210 times the affinity to bind to hemoglobin compared to oxygen. CO is an odorless, tasteless, colorless gas that causes hypaemic hypoxia wherein there is a reduced oxygen carrying capacity of the blood. Carbon monoxide in the blood creates carboxyhaemoglobin (COHb) which prevents oxygen uptake. At sea level, increased levels of COHb cause various symptoms ranging from headache to unconsciousness. At 200 ppm, CO at sea level causes a headache (equivalent to 15-20% COHb content in the body). At higher altitudes, the effects of CO poisoning and altitude hypoxia are cumulative, driving a need for a continuous low-level monitoring of sub-200 ppm levels of CO in aircraft cabins.

Several metal oxide and electrochemical sensors have been operational in household CO detection alarms over the past decade, but none have had the precision to continuously and accurately measure lower ppm levels of CO. Continuous monitoring of carbon monoxide at 35 to 200 ppm levels presents a challenge to any commercially available CO detector technology. Continuous carbon monoxide monitoring is critical in the household, industrial and military sectors. At present, three technologies are used in the manufacture of carbon monoxide alarms. The advantages and disadvantages of each method are outlined below.

Heated Metal Oxide Based Detectors for Carbon Monoxide (CO)

Semiconductor based sensors use heated tin dioxide thin films on a ceramic substrate. CO is oxidized on the high temperature surface. The current increases as the tin dioxide is exposed to carbon monoxide. Microchip controlled electronics detect the change in current and will sound an alarm when levels of CO, as measured by the current, exceed a defined threshold. These sensors operate at high temperatures, greater than 400° C., contributing to high power consumption. This high temperature makes them susceptible to false signals generated by chemically similar analytes. The following is an advantage: inexpensive and easy to produce. The following are disadvantages: high power consumption, slow cycle time; oxygen contamination; susceptible to false positive signals; and requires heating to regenerate system. The above outlined technology remains insufficient to present a complete solution for the continuous detection of carbon monoxide in the lower ppm ranges.

Molybdenum oxide ($MoO_3$) thin films prepared by sol-gel and RF magnetron sputtering processes were previously employed in the development of CO sensors' as described in "Carbon Monoxide response of molybdenum oxide thin films deposited by different techniques," by E. Comini, G. Faglia, G. Sberveglieri, C. Cantalini, M. Passacantando, S. Santucci, in Sensors and Actuators B 68, pp. 168-174 (2000), denoted herein Reference 2. The RF deposited films had a needle-like structure with longitudinal dimension ranging from 200-400 nm. The response was measured by applying a constant potential of 1 V to the sensing layer and registering the resistance with a picoammeter. This CO sensor operates as a chemiresistor. FIG. 8 of Reference 2 shows the dynamic responses of a sol-gel sensor and an RF sputtered sensor at 300° C. to a square concentration pulse of 30 ppm CO. The current changes shown in FIG. 8 of Reference 2 are the picoamp range. This range has the disadvantage that it tends to be almost impossible to record such weak output for a continuous monitor without the use of non-portable, highly sophisticated equipment. The sensor in Reference 2 was operated at 300° C. Heating a sensor substrate consumes much electrical power. This is a disadvantage for a portable device.

Further, research has been continuing in methods of depositing metal oxides. For example, the authors of "Size-selective electrodeposition of meso-scale metal particles: a general method," by H. Liu, F. Favier, K. Ng, M. P. Zach, R. M. Penner, in Electrochimica Acta 47 pp. 671-677 (2001), denoted herein Reference 3, demonstrated that monodisperse nanoparticles of molybdenum dioxide can be grown on a conductive surface using a pulsed voltammetric technique. FIG. 5 of Reference 3 shows the scanning electron micrograph of molybdenum dioxide metal nanoparticles on graphite basal plane surfaces. As shown in that Figure, the nanoparticles have with an apparent size, as indicated by a 1 micrometer scale line, of 100-200 nm. It is also possible to oxidize an existing metal film.

Notwithstanding the above teachings, there is a strong requirement for an alternative technology to heated metal oxide sensors. In particular, there remains a need for gas sensors having low power requirements, broad environmental operating range, fast response time, high selectivity and high sensitivity.

BRIEF DESCRIPTION OF THE DRAWINGS

For a more complete understanding of the present invention, and the advantages thereof, reference is now made to the following description, taken in conjunction with the accompanying drawings, in which.

DETAILED DESCRIPTION

Figure 1:
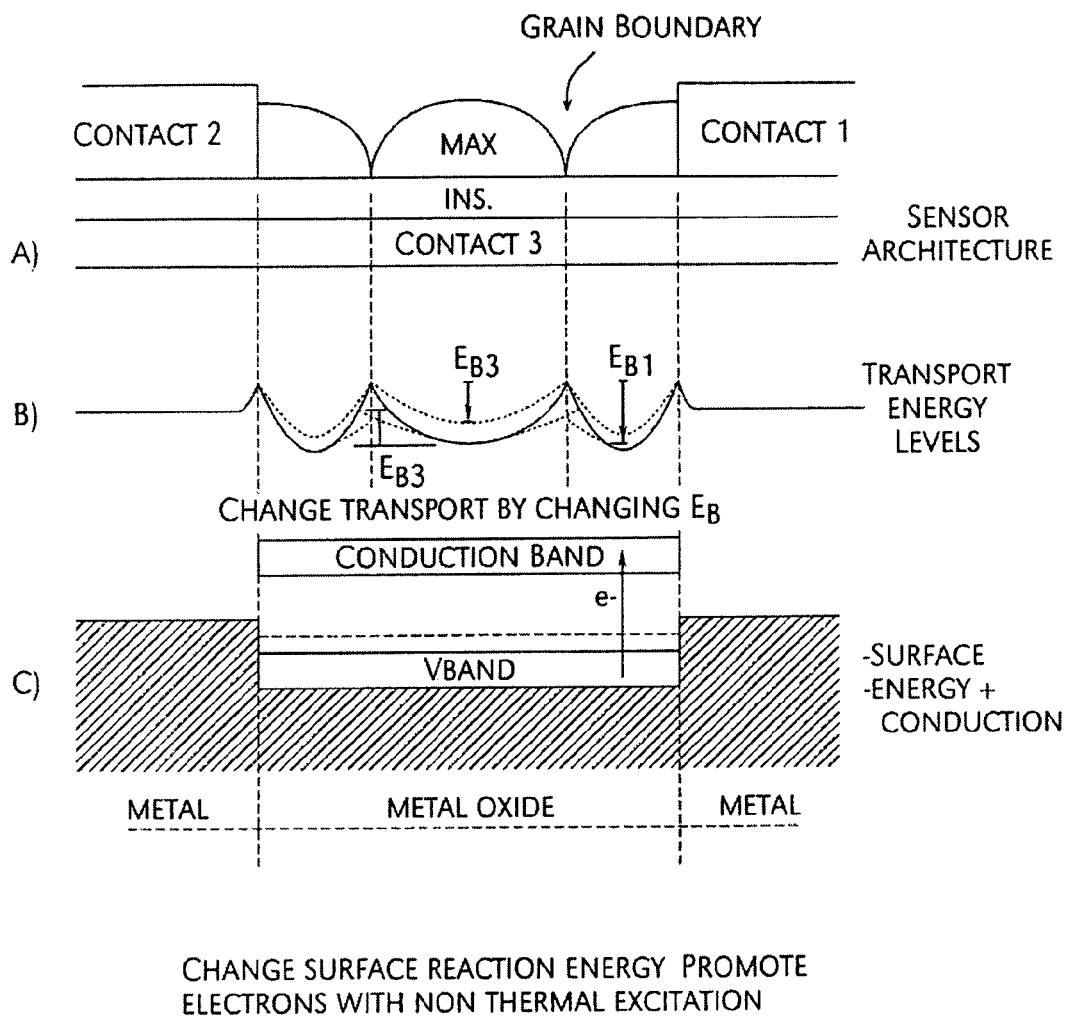
FIG. 1 (1A, 1B & 1C) illustrates tuning the surface energy for reaction and the grain boundary dependent electron transport by application of a gate bias.

Referring now to FIG. 1, FIG. 1 denotes the tunability of the sensor. FIG. 1A shows an exaggerated surface topography of a metal oxide between two contacts. The metal oxide and its contacts are present on top of an insulating layer that separates a third contact. The surface topography creates a grain boundary where conduction of an electron or hole is dominated by the energy barrier to get from one grain to an adjacent grain. Referring now to FIG. 1B, there is an energy barrier associated with the grain boundaries depicted in FIG. 1A. In this embodiment, the conductivity may be tuned through the metal oxide layer. This is accomplished by changing the height of the energy barrier at each grain boundary. When a surface reaction takes place, for example the oxidation of CO to $CO_2$, the electron that is transferred is trapped near the reaction site between these energy barriers. Previous examples have shown that high heat can provide sufficient energy to transport that electron over the energy barrier. In this embodiment, the barrier height is reduced by application of an electrical bias to Contact 3, thereby eliminating the requirement of heat. Referring to FIG. 1C, shown is how the surface reaction energy may be tuned. In FIG. 1C, the metal oxide is semiconducting and has a band gap. This band gap is the energy it takes to promote an electron from the valence band up into the conduction band. Previous examples have demonstrated that high heat is required to create a favorable distribution of electrons within the valence and conduction band for a surface reaction to take place, such as the oxidation of CO to $CO_2$. In this embodiment, the distribution of electrons within the valence and conduction bands is tuned by application of a gate bias.

Figure 2A:
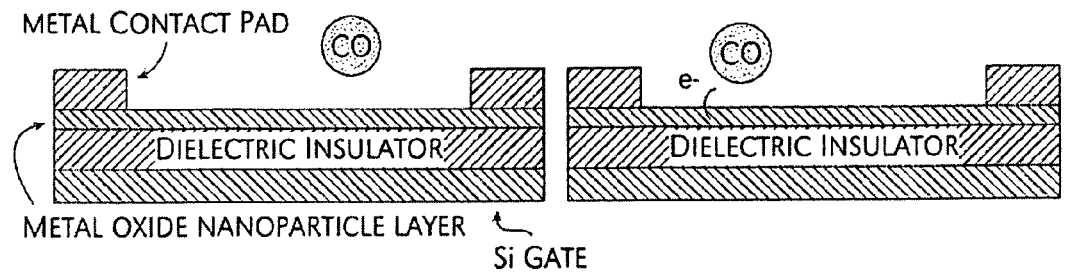
FIG. 2A illustrates an embodiment of the present invention.

Referring now to FIG. 2A, the gas sensor shown in FIG. 2 exemplifies a gas sensor for detecting an analyte gas that includes a first contact (labeled "Metal Contact Pad"), a second contact, a semiconducting layer (labeled "Metal Oxide Nanoparticle Layer"), an insulating layer (labeled "Dielectric Insulator"), a substrate (labeled "Si Gate"), and a third contact (not shown) contacting the substrate. The third contact may serve as a gate contact. The semiconducting layer may include a compound capable of chemical interaction with the analyte gas. Still referring to FIG. 2A, and as described further below, the insulating layer, the semiconducting layer, first contact, second contact, and third contact may be arranged in an architecture predetermined such that the sensor detects a variation in the level of the analyte gas (e.g., CO) as a variation in conductivity between the first and second contacts occurring when a gate voltage is applied across the first contact and the third contact.

Disclosed herein, as an exemplary gas sensor, is a miniaturized, low power, rapid responsive CO sensor based on metal oxide nanoparticle networks applied to thin-film transistor ("TFT") architecture. Certain metal oxides are n-type semiconductors that show an increase in conductance due to the transfer of electrons resulting from oxidation or reduction of an analyte gas. The change in conductance is proportional to the concentration of the analyte gas. The nanoparticle network approach provides considerable improvement in sensitivity and selectivity over the most successful commercial technology of CO detectors based on metal oxide films due to the following reasons. The nanostructured interaction of a metal oxide nanoparticle network provides higher sensitivity compared to commercial detectors. Operation in lower ppm ranges (e.g., 0-200 ppm) is made possible, which cannot be achieved in thick tin oxide thin film based commercial detectors. Further, the metal oxide nanoparticle network can be refreshed by ambient oxygen. Still further, the TFT design enables increased sensitivity due to the built-in gain. The gain comes from a non-linear current vs. voltage curve, characteristic of semiconductors. Yet further, salient characteristics of the proposed device that present an improvement over existing technologies include the following advantages: built-in gain through TFT architecture; on-chip design and integration; fast response and continuous monitoring; built in refresh through chemistry and gate voltage; quantitative response; and time integrated response for cumulative exposure. The TFT architecture can be made using CMOS processing for highly parallel and low-cost manufacturing.

The ability to apply a gate bias can control the sensitivity of the device. Previous work by Fan et al. (Fan, Z. et al. "ZnO nanowires field-effect transistor and oxygen sensing property" *Appl. Phys. Lett.* 2004, (85) 24, 5923-5925, herein denoted Ref. 4) demonstrated an oxygen sensor made from a zinc oxide (ZnO) nanowire field effect transistor. This work showed that the device sensitivity to oxygen changed as a function of gate bias. This device, however, operates with fundamental differences with respect to this invention. The oxygen in this device is physically adsorbed to the ZnO surface. The oxygen adatom (adsorbed atom) is electronegative and removes electron density from the semiconductor changing the distribution of current carriers. This change in carrier concentration is the same thing that happens when a gate bias is applied to any semiconductor and is by definition a change in current by field effect. This previous devices operates as a ChemFET. Their device will not operate in ambient environmental conditions due to surface saturations at normal oxygen concentrations. It is not a sensor, but rather a physical change in transistor response due to a change in environment.

The present invention operates via chemical reactions at a metal oxide surface. These chemical reactions can add (through oxidation) or remove (through reduction) electrons from the semiconducting layer of the sensor. The change in number of electrons will change the current through the device. The removal of electrons will always cause a change in current even if the material is a poor semiconductor whereas oxygen adsorption changing electron density or distribution will not.

Previously, Dalin (Dalin, J. "Fabrication and characterization of a novel MOSFET gas sensor" Final Thesis at Linkopings Institute of Technology, Fraunhofer Institute for Physical Measurement Techniques, Frieburg, Germany, Jun. 5, 2002, LiTH-ISY-EX-3184, herein denoted Ref. 5) showed that a gate bias can modulate the current through a tin oxide ($SnO_2$) gas sensor operated at 200° C. or 280° C. This is a heated sensor. While the current level through the sensor changed, the sensitivity did not. For example, Ref. 5, FIG. 6.5 shows the actual current values to different concentrations of CO at variable gate bias. This figure shows a noticeable change in current of the sensor response at each gate bias. In Ref. 5, FIG. 6.6, the response of a heated $SnO_2$ sensor to CO is plotted as initial current over actual current. In this figure, there is a measurable, but small change in sensitivity as a function of gate bias. If one inspects the change in response, one can see that the baseline of the response changes nearly the same as the exposed response. This indicates that the gate bias changes the current level through the sensor but does not increase the sensitivity. The sensor of Ref. 5 did not operate at lower temperatures.

The gated metal oxide sensor of the present invention does not require heat for operation. This gated metal oxide sensor operates from −60° C. to greater than 100° C. It demonstrates an increased response at lower temperatures.

Technical Approach—Chemistry:

Metal oxide chemistry is a driving force for this invention to sense an electron transfer from a surface reaction of an analyte gas. The analyte gases include, but are not limited to, carbon monoxide (CO) and other electron donating and or electron accepting species. The success of the sensor requires a maximized semiconductor response in the metal oxide. Any metal oxide thin film/nanoparticle system is deemed suitable with the present invention, but a more specifically transitional metal oxide such as molybdenum oxide ($MoO_3$) is used due to its unique properties towards CO. Metal oxides exist in several forms. For example, molybdenum oxide could be MoO, $MoO_2$, $MoO_3$ depending on the oxidation state of the metal. The invention cites $MoO_3$ as a specific example, but the invention is applicable to other oxides of molybdenum. $MoO_3$ is an n-type semiconductor that will oxidize CO through electron transfer, which causes a measurable change in resistance. Molybdenum trioxide contains molybdenum in its hexavalent state. Hexavalent molybdenum has no electrons in its 4d orbitals. As a result, oxidation of +6 carbon monoxide involves an electron transfer of an electron from CO to $Mo^{+6}$. Following this initial electron transfer step, several reaction pathways are possible for the subsequent oxidation of carbon monoxide to carbon dioxide. Most likely, these pathways involve rapid, free radical chain steps, which translate to a fast, responsive sensor.

The invention includes, but is not limited to, molybdenum oxide nanoparticles for CO detection. Molybdenum oxide presents certain unique properties suitable for the present invention. Other metal oxides may be used with solid state sensor design, but none have equivalent properties to molybdenum oxide. The two other metals in Group 6B are Chromium (Cr) and Tungsten (W). They have a similar chemistry to molybdenum oxide. The top of the period ($CrO_3$) will be more reactive. This reactivity comes at a cost. The more reactive species will create a more stable product increasing the difficulty of reversing the reaction, i.e., refreshing of the sensor. The increased reactivity will also reduce the sensors selectivity. Conversely, the bottom of the row ($WO_3$) will be less reactive reducing sensitivity but more easily reversed. Molybdenum oxide has the highest reactivity combined with the greatest ease of reversibility. Metal oxides outside Group 6B have not demonstrated the required sensitivity or selectivity towards CO. This includes tin dioxide.

Chemical interferences to the proposed sensor systems, such as water vapor, are not problematic. Other possible contaminants in a vehicle or in an industrial or household environment such as carbon dioxide, nitrogen dioxide or saturated hydrocarbons are not expected to interfere with this sensor system. They will not bind to $MoO_3$ through an electron transfer, and will therefore not produce a signal. It is possible to design a metal oxide material that would be specific and selective to a particular analyte. At the same time, it is possible to design a metal oxide material that will exclude sensitivity of a particular analyte. Additionally, a gate bias applied to a metal oxide material could enhance selectivity toward chemically similar analytes.

The use of spherical nanoparticle films has several advantages compared with nanoparticles of other morphologies. Spherical nanoparticles have an increased percentage of active surface atoms (diameters ranging from 5-300 nm). The atoms in the middle of the particle, called the "bulk," do not contribute electronically to any reactions or binding events.

When a reaction or binding event takes place, these surface atoms make a greater contribution to the overall electronic structure of the nanoparticle. This increased contribution translates directly into an increased signal. Quasi-spherical nanoparticles have similar surface to bulk ratios. This would include a nano-"bump" on a substrate or small grains of material on a surface. Additionally, very thin-films of metal oxides will show increased sensitivity due to high surface to bulk ratios. Maximum sensitivity should occur at a thickness near the Debye-length for the particular semiconducting material; however, overall conductivity must also be considered.

TFT Sensor Design

Due to the semiconducting properties of $MoO_3$, the invention employs a thin-film transistor (TFT) architecture to maximize the signal output of the CO sensor. Molybdenum Oxide is an n-type semiconducting material. This means that conduction through the material can be manipulated by a third terminal contact commonly called a gate. Because it is an n-type semiconductor, the resistance will decrease as we move to a positive gate voltage. An electron transfer from the oxidation of CO to $CO_2$ will increase the number of electrons in the $MoO_3$ film, therefore increasing the number of carriers and also the current through the device. This is effectively the same as applying a positive gate voltage.

Referring again to FIG. 2, FIG. 2A illustrates a metal oxide semiconductor thin film transistor for CO detection. An electron transfer takes place when CO is oxidized on the surface of the metal oxide. This surface reaction changes the carrier concentration of the n-type semiconductor and is measured as a change in current.

The semiconducting nature of the $MoO_3$ contributes to an increased sensitivity in the sensor. The TFT architecture has inherent gain, which is to say that a very small change in gate voltage (for example an electron transfer caused by an oxidation of CO) creates change in current. An electron transfer event from an oxidation of a gas like CO into the metal oxide nanoparticle framework is depicted in FIG. 2A. As seen in FIG. 2A, this electron transfer event causes a change in current that can be up to several orders of magnitude depending on the slope of the current vs. gate voltage curve. This curve is based on an n-type semiconducting material. The invention can be manipulated for a reducible gas by making the semiconducting channel p-type. In this type of device, the surface would provide an electron to allow an oxidized chemical species to be reduced. Changing from n-type to p-type would require a change in the chemistry of the metal oxide by changing the base metal, alloys of other metals or doping with small amounts of additional materials.

Figure 2B:
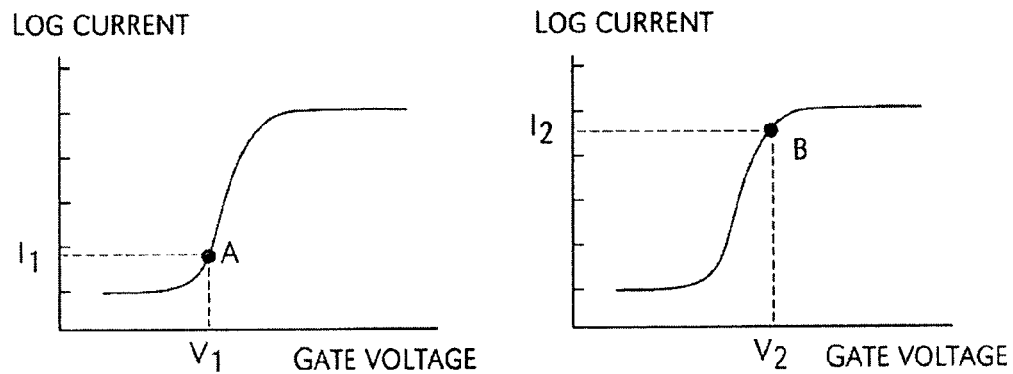
FIGS. 2B and 3 plots are illustrating the sensitivity based on internal amplification of a gas sensor according to an embodiment of the present invention.

Referring now to FIG. 2, FIG. 2B illustrates Current vs Gate Voltage for an n-type semi-conductor showing the high inherent change in current ($\Delta I$) by changing a small gate voltage ($\Delta V$) due to the electron transfer from CO.

Figure 3:
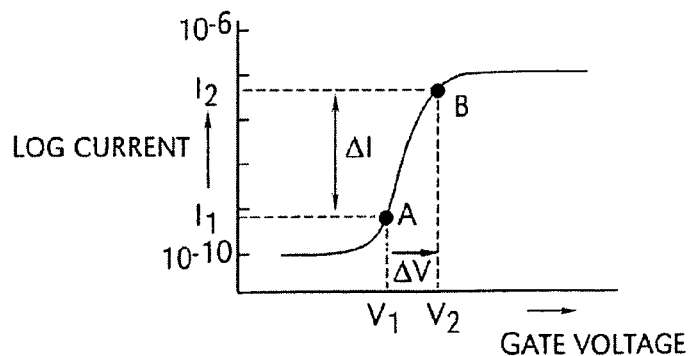

As seen in FIG. 3, movement from point A to point B requires only a small change in gate voltage. Thus a small change in voltage results in a large change (nearly three orders of magnitude) in current, thereby increasing the inherent gain ($\Delta V/\Delta I$). This signal amplification allows for unmatched levels of sensitivity, otherwise not achievable in a chemresistor transduction. In addition, manipulation of the gate voltage allows the sensor to operate in the most sensitive area of the I-V curve, i.e., where the slope, and therefore the sensitivity of the device is the steepest.

The TFT architecture may be processed by a method that includes electrochemically depositing $MoO_3$ nanoparticles on a conductive substrate as described below. Further, the metal oxide may be deposited by a solution method. Still further, the metal oxide may be grown by oxidizing a thin metal film or metal nanoparticle film.

The present inventors contemplate growing nanoparticles with two parallel approaches using, for example, a Gamry Potentiostat with PC interface. In approach I the process includes direct deposition of the nanoparticles on a conductive substrate, followed by transforming a surface portion of the conductive substrate into an insulating layer. In approach I, the two step process includes indirect deposition of the nanoparticles on a conducting substrate and removal of the nanoparticles from the conducting substrate followed by deposition of the nanoparticles on an insulating substrate. While the indirect and direct deposition are described by way of example as electrochemical growth it will be understood that alternative deposition methods known in the art are contemplated, for example sputtering, thermal evaporation, electron beam evaporation, and the like. Further, in accordance with the deposition method, initial deposition may occur on any suitable surface, selecting from among conductors, insulators, and semiconductors.

Most transition metal oxides will catalytically react with gas analytes by a reduction or oxidation reaction at high temperatures. Each redox reaction occurs at a specific energy. These redox reactions will add or remove electrons from the films resulting in a measurable change in conductivity. The change in conductivity of these sensors is governed by equation (1):

$$G=G_o\exp\{(\Delta_\chi-\Delta\phi)/kT\};$$

Where G is the conductivity, $\chi$ is electron affinity and $\Phi$ is the work function. This equation states that the change in conductivity is a function of the change in work function and the change in dipole moment when a gas species reacts on the surface. Until recently, metal oxide sensors were made by sol gel processing methods which produced large grain sizes creating a large energy barrier for electron transport between the individual grains. High temperatures (>250° C.) are required for electron transport over these energy barriers. This is predicted by equation. (1). There is no known prior art for manipulating the electron affinity or the work function of the material. Most transition metal oxides are semiconducting that will allow a change in conductivity through application of an external electric field such as a gate bias (electronic modulation). The application of a gate bias affects equation (1) in ways that temperature cannot. First, it changes the Fermi-level energy, which results in an induced change in work function $\Phi$. Second, due to charge depletion in the semiconducting layer, there is a shift in electron affinity $\chi$ at the external surface. Both of these affect the nature of interaction of gas analyte with the sensor surface, and the electron transport through the metal oxide is increased. Both $\Phi$ and $\chi$ are independent of temperature making the present invention far superior to heated metal oxide systems. While the innovation of temperature independence is remarkable enough, further significance of this architecture lies in the interdependence of electron affinity $\chi$ and work function $\Phi$. These two terms define the physics of a tunable sensor platform that may be designed to be selective towards any analyte. One only need to change the surface chemistry ($\Phi$) and change the gate voltage ($\chi$). The present invention will use this innovative technology to overcome any thermal requirements for metal oxide sensors.

Figure 11:
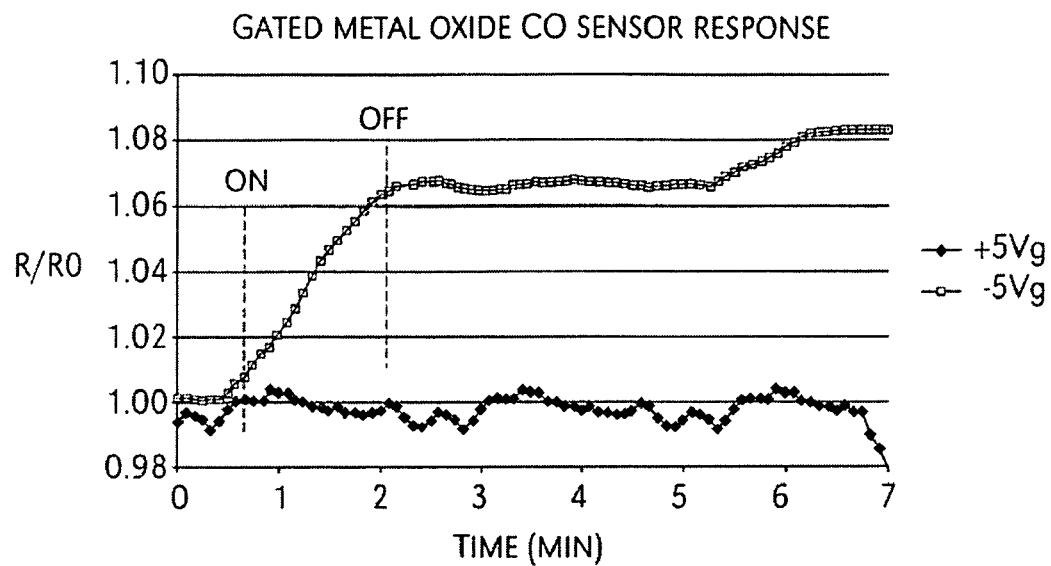
FIG. 11 is a plot of the response of an exemplary gas sensor according to an embodiment of the present invention.

The semiconducting nature of metal oxides allows for oxygen vacancies in the lattice structure of the material. It is these vacancies that allow for oxidation reactions to occur at the film surface. The oxidation reaction generates an electron transfer from the analyte into the film. This new electron is temporarily trapped in the metal oxide lattice and can then be transported to an electrode and measured as a change in conductivity. The large band gap associated with these metal oxide films typically drives a high temperature process for the catalytic oxidation and detection. For example, most $SnO_2$ sensors operate in a temperature range above 350° C. This thermal energy increases the surface activation energy of the reactive sites, promotes facile oxidation of the analyte and improves electron transport to the electrodes for measurements. In the present invention, the application of a gate bias lowers the energy barrier at the grain boundary of the metal oxide to enable electron transport at a unique gate voltage for a specific metal oxide-analyte combination. FIG. 11 shows an increase in sensor current when exposed to CO at different gate voltages. FIG. 11 shows the gated sensor responding to CO at −5V and not responding at +5V. This gate voltage modulation serves as a basis for forming an electronic signature for multiple gases by rippling the gate voltage for a specific gas or a number of gases. A response to a gas can be obtained at one gate voltage and by changing the gate voltage (for example for CO from −10 to +10 V) can be combined into a database for a signature pattern for the gas.

Furthermore, by varying the metal oxide chemistry and the gate voltage a broad spectrum of gases including toxic vapors, volatile organic compounds, chemical warfare agents, vapors from biowarfare agents, hydrocarbons, and smoke can be detected.

Figure 4:
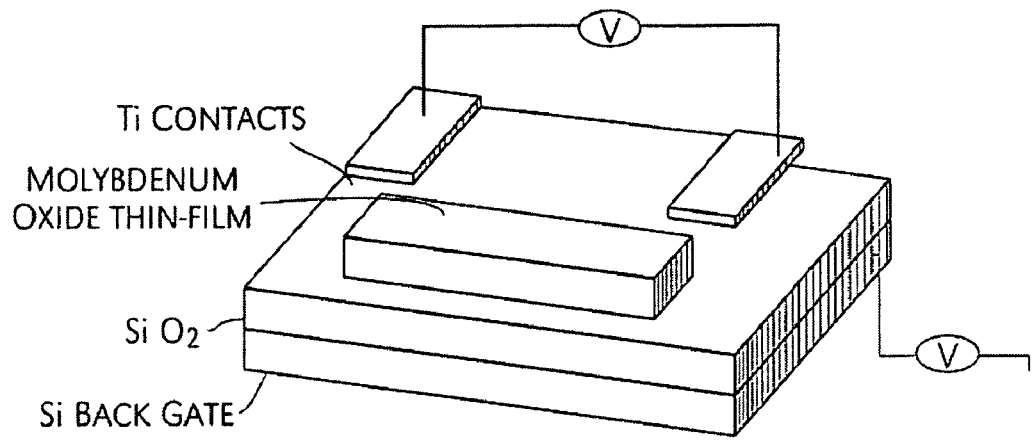
FIG. 4 illustrates a gated metal oxide sensor architecture.

By taking advantage of the semiconducting properties of $MoO_{3-\delta}$, the sensor incorporates a thin-film transistor (TFT) architecture to maximize the signal output. $MoO_{3-\delta}$ is an n-type semiconducting material. This means that the position of specific electronic energy levels within the material can be tuned by a third terminal contact commonly called a gate. An example of the sensor architecture is shown in FIG. 4. The gate regulates position of the Fermi level of the semiconducting film. This change in energy allows electrons to pass from donor band generated by oxygen defects into a conduction band. $MoO_{3-}$-based TFTs do not show an appreciable change in current when a gate voltage is applied which is expected for a normal semiconductor material. What is observed is a change in the response of the sensor. The change in the position of the Fermi-energy level by the gate bias allows for facile oxidation of CO. The result is a faster, more sensitive sensor.

An advantage of the sensor over a conventional thin-film metal oxide sensor is that it does not require an on-chip heater. This is extremely important when one considers power consumption for a portable detector. The traditional commercial tin oxide-based sensors require heating to 300° C. or higher before the catalytic properties that allow for the oxidation reaction of CO are activated. The presence of the catalyst changes the position of the Fermi level within tin oxide-based sensors. This change in the Fermi energy changes the surface charge of the metal oxide and therefore changes the conductivity of the material. Instead of utilizing heat to achieve thermal activation of the surface and reaction of the metal oxide with CO, an applied gate voltage is used to tune the surface states within the sensor of the present invention.

The efforts involving the polymorph of molybdenum oxide which is CO-selective can be summarized as follows:
- $\beta$-$MoO_{3-\delta}$ is sensitive and selective to CO
- $\beta$-$MoO_{3-\delta}$ is difficult to synthesize due to its metastable character and due to limitations in the available deposition techniques
- $\beta$-$MoO_{3-\delta}$ exists as a nanocrystalline phase within the thin films
- Synthesis of the thermodynamically stable phase $\alpha$-$MoO_{3-\delta}$ is not desirable
- It is difficult to achieve reproducible results for both the synthesis and the gas-sensing properties of the different films The details of the synthesis, the structural, electronic, and gas sensing properties of the numerous thin films containing $MoO_{3-\delta}$ are found below. The various challenges encountered and the attempts which were made to overcome them are also presented.

Structural and Electronic Properties of $MoO_{3-\delta}$

Figure 5A:
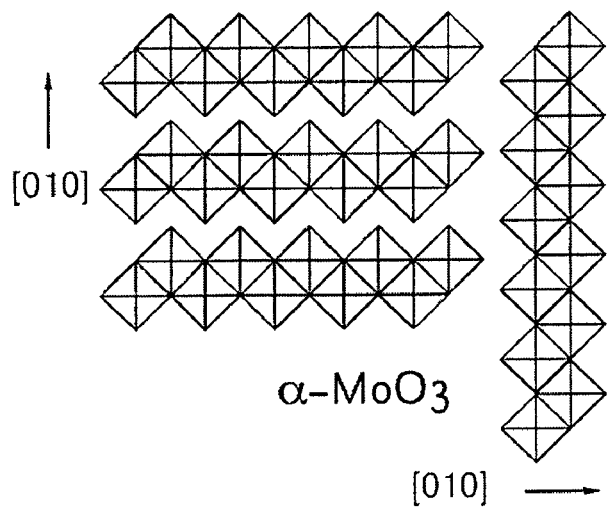
FIGS. 5A and 5B illustrate crystal structures of Lamellar $\alpha$-$MoO_{3-\delta}$ and three dimensional $\beta$-$MoO_3$ viewed along the [100] axis.
Figure 5B:
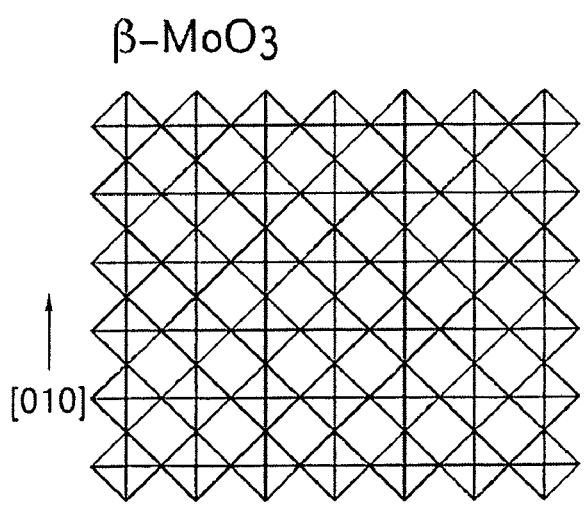

Molybdenum forms a variety of oxides which exhibit different valence states, crystallographic structures, electronic behavior, and variable oxygen coordination. Single-valent $MoO_2$ is an n-type metal and has a monoclinic-distorted futile structure (space group $P2_1/c$) where infinite linear chains of edge-sharing $MoO_6$ octahedra which run along the pseudotetragonal axis are linked together via corner sharing along the other two directions. Its lattice parameters are a=5.611 Å, b=4.856 Å, c=5.628 Å, $\beta$=120.9°, and V=131.58 Å$^3$. Hexavalent Mo is found only in the crystallographic phases $MoO_3$ and $MoO_3 \cdot xH_2O$ (x=1, 2) where the former has three (3) distinct polymorphs, the thermodynamically stable $\alpha$-$MoO_3$ and the metastable phases $\beta$-$MoO_3$ and h-$MoO_3$. As shown in FIG. 5A, $\alpha$-$MoO_{3-\delta}$ is an n-type semiconductor with an electronic band gap $E_g$ between 2.9 and 3.2 eV and crystallizes in parallel layers of edge-shared, corrugated sheets of $MoO_6$ octahedra where each layer is separated by a van der Waals gap of ≈7 Å. It is orthorhombic with space group Pbnm and has lattice parameters a=3.963 Å, b=13.855 Å, c=3.696 Å, and V=202.94 Å. As shown in FIG. 5B, $\beta$-$MoO_{3-\delta}$, on the other hand, is composed of a three-dimensional network of corner-shared $MoO_{6/2}$ octahedra and has a monoclinic-distorted $ReO_3$ structure with space group $P2_1/c$ and lattice parameters a=7.122 Å, b=5.374 Å, c=5.565 Å, $\beta$=91.88°, and V=212.99 Å. Thin films of $\beta$-$MoO_{3-\delta}$ show n-type semiconducting behavior and are more conducting than those of $\alpha$-$MoO_{3-\delta}$ due to the existence of a higher concentration of mobile electrons in a donor band, associated with oxygen vacancies, ≈0.5 to 1 eV below the Mo 4d conduction band. Bulk samples readily transform into the thermodynamically stable $\alpha$-$MoO_3$ at temperatures between 350 and 380° C. although this phase transformation temperature is greatly suppressed in thin films to values less than 250° C. Other molybdenum oxides which exist are typically mixed-valent $Mo^{5+/6+}$, low-dimensional metallic conductors which crystallize in various structures that contain corner-sharing or edge-sharing $ReO_3$-type chains Thin films of $MoO_{3-\delta}$ were initially generated on a hotplate by thermally annealing in air, device coupons patterned after mask set with 45 to 150 Å of e-beam evaporated Mo metal, for 2 to 4 days. As described earlier, the thermal oxidation of these films was monitored by observing the evolution of the device's electrical resistance by directly monitoring the drain current $I_D$ at a fixed, applied source-drain dc bias of 0.1 V. Initially, the drain current $I_D$ for an as-deposited Mo film less than 100 Å thick was typically 0.1 to 0.4 mA. At intermediate stages of oxidation, $I_D$ dropped to values between 2 and 30 µA, and upon complete oxidation, $I_D$ varied between 5 and 60 nA.

The thickness of the $MoO_x$ film on different devices at the various stages of thermal oxidation were also measured with the KLA Tencor AS 200 stylus profilometer and compared with the original thickness of the as-deposited Mo film. Devices which contained $MoO_x$ generated at intermediate stages of oxidation where $I_D$≈5 to 10 µA, displayed a 4- to 4.5-fold increase in the film thickness, which is consistent with the formation of a majority of the phase $MoO_2$. However, a 6.2- to 6.6-fold increase in film thickness, when compared to the original as-deposited Mo film, was observed for devices which gave an $I_D \approx 5$ to 30 nA, which points to the formation of almost completely oxidized $MoO_{3-\delta}$.

Figure 10:
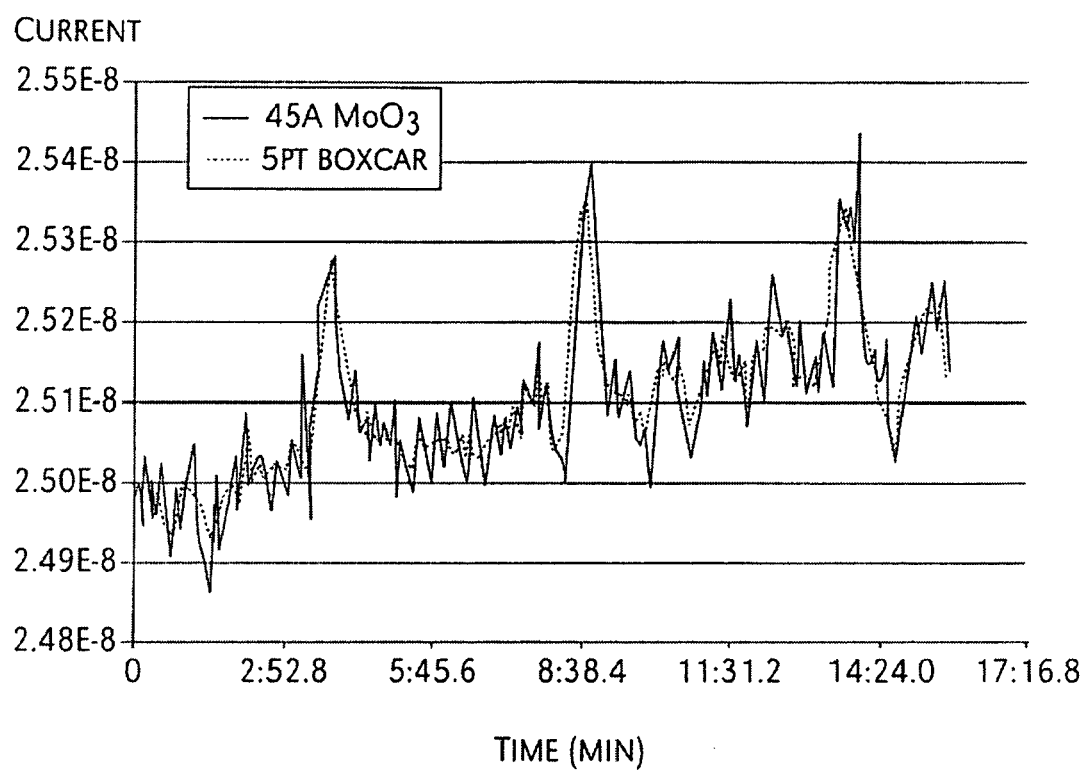
FIG. 10 illustrates a sensor response by an embodiment of the present invention to three successive deliveries of 200 ppm CO.

Furthermore, an initial CO sensitivity test was then performed on these devices at the probe station by exposing the device to cycles of air and 200 ppm CO at fixed flow rates and observing the changes in their drain current $I_D$ first at an applied dc gate bias $V_G=0$ V and then at various positive and negative values. An example of this initial sensitivity is shown in FIG. 10. Some of the devices which were responsive to CO were then cleaved off the main device coupon and mounted onto T05 headers for further CO testing. Other CO-responsive devices were then sent with devices which were unresponsive to CO together with devices which were at intermediate stages in their oxidation for surface characterization with Microprobe Raman Spectroscopy (M-RS) and Field Effect Scanning Electron Microscopy (FE-SEM).

Figure 7:
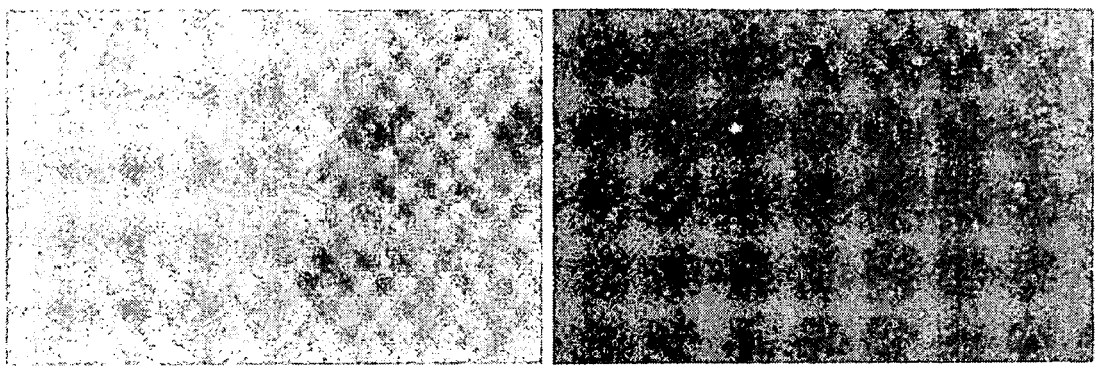
FIG. 7 shows digital images of FE-SEM micrographs of the surface of (left image) a device that shows no response to CO and (right image) one that responds to CO.
Figure 8:
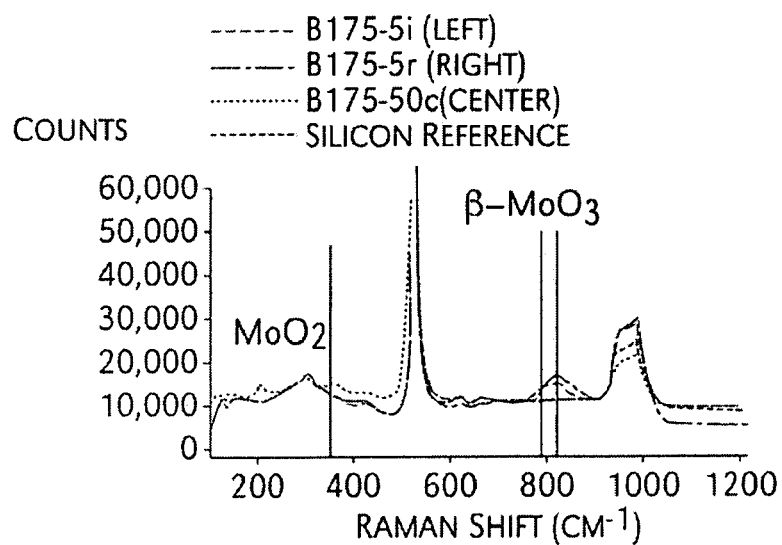
FIG. 8 shows microprobe Raman Spectra obtained from various samples, where the top graph shows the target $\beta$-$MoO_2$ as it is formed through oxidation of the intermediate phase $MoO_3$, and where the bottom graph shows a thin film that contains a mixture of both $\alpha$-$MoO_{3-\delta}$ and $\beta$-$MoO_3$.
Figure 8:
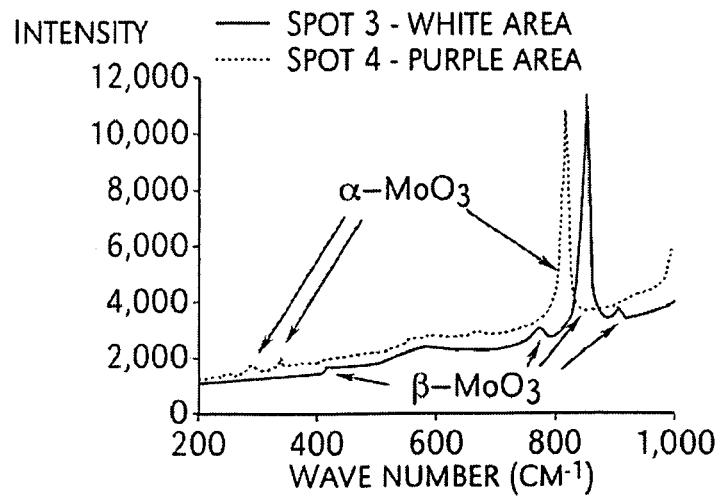
Figure 9:
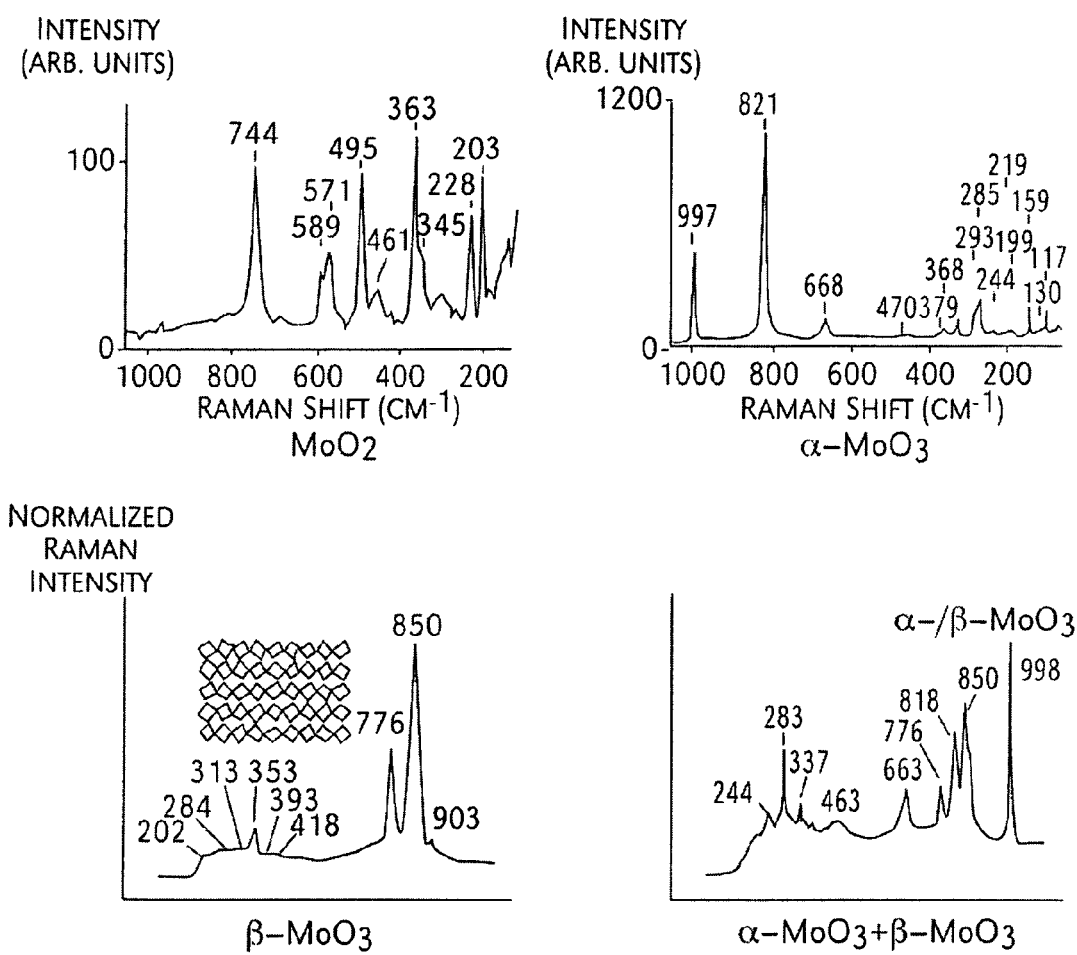
FIG. 9. illustrates Raman Spectra of $MoO_2$, $\alpha$-$MoO_{3-\delta}$, $\beta$-$MoO_3$, and a mixture of $\alpha$- and $\beta$-$MoO_3$.

Referring to FIG. 7, FE-SEM micrographs of devices which were unresponsive to CO clearly showed the existence of submicron to micron-sized needle-like crystallites embedded in their surfaces whereas scattered regions of nanocrystalline domains in a somewhat poorly crystalline matrix were observed on the surfaces of all CO-responsive devices. The micrographs for devices at intermediate stages of oxidation showed very little surface topography and morphology. M-RS analysis over multiple spots on the surfaces of devices which were unresponsive to CO, (left image in FIG. 7), revealed the unmistakable presence of 100% $\alpha$-$MoO_{3-\delta}$, a phase which has a needle-like or acicular habit due to its orthorhombic structure. However, in CO-responsive devices, this analysis revealed a large percentage of the phase $\beta$-$MoO_{3-\delta}$, found in the nanocrystalline domains, together with some $\alpha$-$MoO_{3-\delta}$, (see right image in FIG. 7). The result of these analyses was similar to those of Mc Evoy et al. (T. McEvoy and K. J. Stevenson, Langmuir 21, 3521 (2005)) who thermally annealed electrodeposited films of hydrated molybdenum oxides and observed with SEM, M-RS, and conductive-probe atomic force microscopy (CP-AFM), poorly conducting microcrystalline regions within their films which contained $\alpha$-$MoO_{3-\delta}$ and regions of nanocrystalline domains which contained $\beta$-$MoO_{3-\delta}$ and were seven orders of magnitude more conducting. Furthermore, M-RS analysis on the surfaces of devices at intermediate stages of oxidation showed lines which were consistent with the phase $MoO_2$ (see FIG. 8). Clearly, the oxidation of Mo thin films proceeds via the formation of the intermediate phase $MoO_2$ before completely oxidizing to $MoO_3$. The Raman spectra of the various $MoO_x$ phases from the literature are shown for comparison in FIG. 9.

Despite this effort, all attempts to reproducibly generate devices on the hotplate which consistently responded to CO proved to be unsuccessful. Even devices which initially demonstrated great sensitivity to CO in the first few weeks no longer responded to CO after that.

First, the surface of the as-deposited Mo metal thin film was cleaned with a snow jet before any annealing of the coupon took place. Second, vacuum annealing was implemented which effectively removed any moisture from the clean metal surface and therefore inhibited the formation of the phase $MoO_{3-\delta} \cdot xH_2O$ ($x<2$), which would have, upon thermally annealing in $O_2$, produced a large majority of the non-CO-selective phase $\alpha$-$MoO_{3-\delta}$ and a very small amount of the desirable phase $\beta$-$MoO_{3-\delta}$. Third, thermal oxidation of the devices took place in a tube furnace in either a flowing $O_2$ atmosphere or in a static $O_2$ atmosphere pressured to values between 1.2 and 1.6 atm in the narrow temperature range 175 to 225° C. for 2 to 6 hours and then cooled at 2° C./min in the same atmosphere. This approach has unique advantages of (1) exposing the devices to a constant low humidity, (2) ensuring reproducibility of conditions for devices which need to be annealed under the same conditions, (3) controlling the heating and cooling rates to which the devices are exposed, and (4) having the flexibility of increasing the $O_2$ pressure to above 1 atm during annealing. Fourth, the mask set was modified to greatly enhance the sensitivity of the device by now incorporating an array of interdigitated electrodes of width 26 μm and pitch 20 μm for each device. In this new mask set, the sensing material was now deposited onto this interdigitated electrode array. Further modification to produce a new mask set, occurred by the introduction of Cr/Au bonding pads onto the source (S), drain (D), and gate (G) contacts as well as a large reduction in the device dimension. Fifth, a comprehensive database was established which contained detailed information about the device coupons before and after they were annealed. Many of the samples would initially respond to CO and then become non-responsive within a time period approaching one week. This is expected due to thermodynamic conversion from the beta- to the alpha-phase molybdenum oxide.

While the challenges to stabilize the CO-selective phase $\beta$-$MoO_{3-\delta}$. were being overcome, other metal oxides which are sensitive to CO were being investigated. While the concept was initially invoked for implementation with CO sensing in $\beta$-$MoO_{3-\delta}$, theoretically it is applicable to any semiconducting metal oxide material. The next candidate which was chosen for CO sensing has been the most studied of all gas-sensitive oxides, tin (IV) oxide ($SnO_2$). The major disadvantage of $SnO_2$ is its cross-sensitivity patterns. Published literature show $SnO_{2-\delta}$, is sensitive not only to CO but also to approximately 40 additional analyte gases.

Microprocessor Development and Device Integration:

The microprocessor developed as a part of this invention will have the ability to manipulate the gate voltage, measure current through the CO sensor, compute a CO concentration, and drive a digital display and output to an alarm. The device box will likely contain both a piezo-based audible alarm and an LED based visual alarm. The microprocessor will be required to run more than one input channel. An inactive reference sensor will be incorporated in the device to cancel aging and temperature drift. The reference channel will be measured along with the active sensor during each sampling cycle. Data samples are averaged to filter noise and converted to CO concentration levels. The on-board LCD display will be updated every 20 seconds or less.

Figure 6:
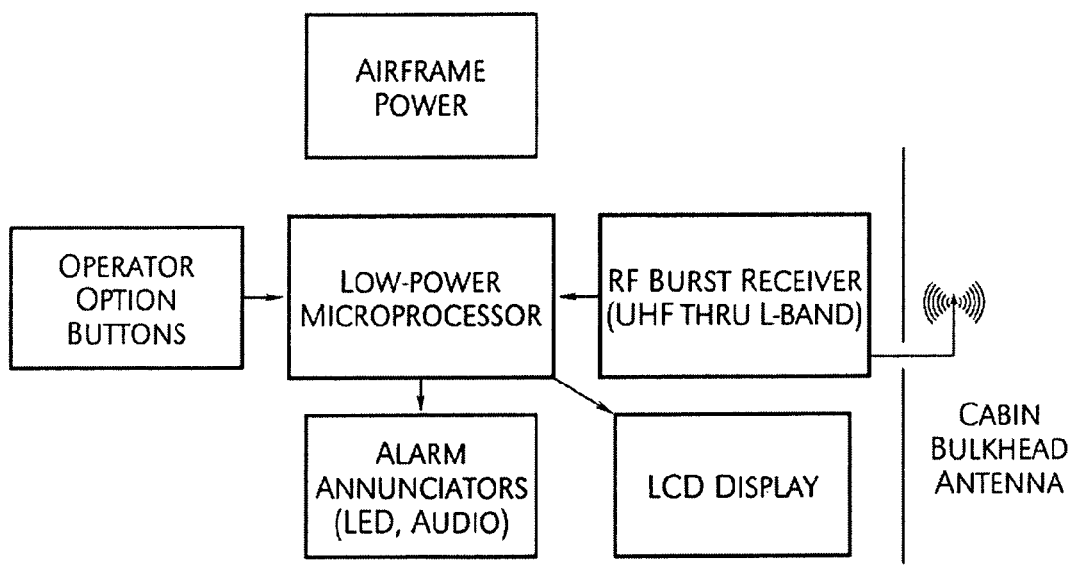
FIG. 6 is a schematic diagram illustrating a gas sensor for remote applications according to an embodiment of the present invention.

Referring now to FIG. 6, FIG. 6 illustrates radiofrequency (RF) integration for remote applications.

The same architecture will be fully compatible with a low-power RF link for remote readout. Referring again to FIG. 6, FIG. 6 shows a possible arrangement. The software capability would handle normal "I'm alive" and battery status reporting, as well as change-of-measurement readout. An approximate duty cycle of 0.1% activity is assumed with reporting of CO changes occurring at approximately 10 second intervals. This holds total power consumption to approximately 2 mW, occurring at the 0.1% interval. This low average power consumption enables long battery life.

The present invention will be more easily and fully understood by the following example. The example is representative of a gas sensor in accordance with one embodiment of the present invention.

EXAMPLE

A sensor was prepared by growing molybdenum trioxide, as an exemplary sensing compound, in a thin film arranged as part of a thin film transistor architecture. The growth was via electron beam evaporation of molybdenum, followed by thermal oxidation of molybdenum. The structure of the film was characterized using a scanning electron microscope (SEM). The film had a nanoparticle structure. The deposited metal film had a thickness of less than 20 nm.

FIG. 11 shows the response of the sensor to a continuous flow of carbon monoxide at 50 ppm inside a sealed chamber. The sensor was operated at room temperature. The response was measured as the normalized ratio of R, the resistance in the presence of carbon monoxide, to Ro, to the resistance in the absence of carbon monoxide, as a function of time. The response was determined for two different values of gate voltage, +5 V, and −5 V. The lines marked ON and OFF indicate the dose of CO being turned on and off. The upper curve (−5Vg) shows a response to CO. The lower curve (+5Vg) shows no response to CO. The results demonstrate that the response of the sensor may be tuned by varying the gate voltage.

Figure 12:
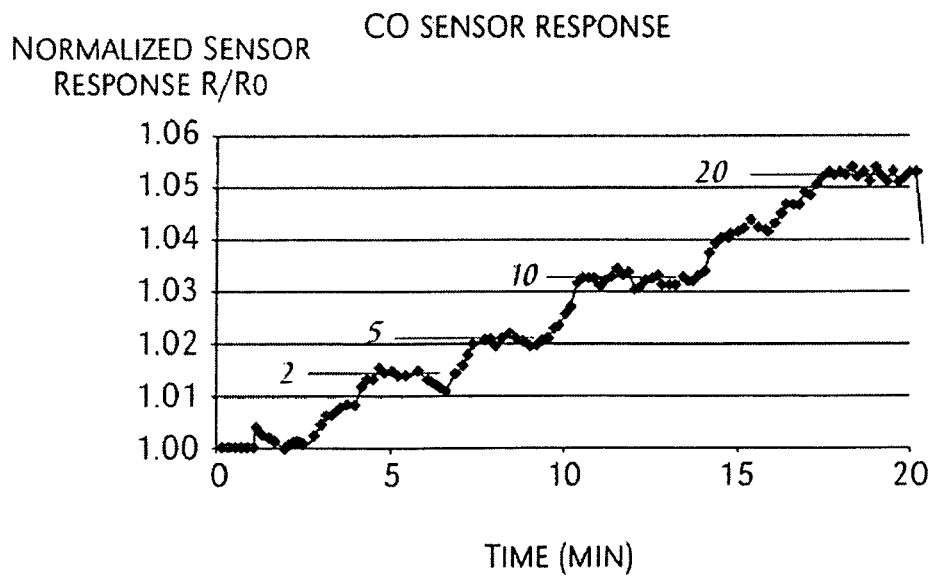
FIG. 12 is another plot of the response of an exemplary gas sensor according to an embodiment of the present invention.

FIG. 12 shows the response of the same sensor to a continuous stream of carbon monoxide at increasing levels of concentration of 2 ppm, 5 ppm, 10 ppm, and 20 ppm. The sensor was operated at room temperature. The response was measured as the normalized ratio of R, the resistance in the presence of carbon monoxide, to Ro, to the resistance in the absence of carbon monoxide, as a function of time. The results demonstrate the sensitive response of the sensor to low levels of gas. The response to CO is linear.

These above-described results further demonstrate that the requirement of heating the sensor is eliminated so as to operate at room temperature (22 degrees C.) by using a gate bias.

The present inventors have discovered that operation of at temperatures lower than room temperature is also possible, for example −60 degrees F. Thus, the sensor may operate at atmospheric temperatures encountered from ground level to up to 40,000 feet, and thus is adapted for use in an air plane or other high altitude application. Thus, a method of operating the sensor may include adjusting the gate voltage according to the temperature.

The present inventors have further discovered that the gate bias can be tuned to different analyte gases at a wide range of concentrations.

Thus, a method of operating a sensor according to an embodiment of the present invention may include tuning any one or combination of the gate bias and the sensing compound so as to select the analyte.

Although the present invention and its advantages has been described in detail, it should be understood that various changes substitutions and modifications can be made herein without departing from the spirit and scope of the invention as defined by the appended claims.

What is claimed is:

1. A sensor for detecting the presence of an analyte gas, the sensor comprising:
a substrate;
an insulating layer;
a semiconducting layer separated from the substrate by the insulating layer;
a first contact contacting the semiconducting layer;
a second contact contacting the semiconducting layer; and
a third contact contacting the substrate;
wherein the semiconducting layer comprises beta-molybdenum oxide capable of chemical interaction with carbon monoxide;
wherein the third contact is a conductive layer on the substrate separated from the semiconducting layer by an insulator; and
wherein the insulating layer, the semiconducting layer, first contact, second contact, and third contact are arranged in an architecture predetermined such that the beta-molybdenum oxide detects a variation in the level of the carbon monoxide as a variation in a current between the first and second contacts occurring when a voltage is applied across the first contact and the third contact.

2. The sensor according to claim 1, wherein the chemical interaction comprises electron transfer.

3. The sensor according to claim 2, wherein the electron transfer comprises electron donation by the carbon monoxide to the beta-molybdenum oxide.

4. The sensor according to claim 2, wherein the electron transfer comprises electron withdrawal by the carbon monoxide from the beta-molybdenum oxide.

5. The sensor according to claim 2, wherein the beta-molybdenum oxide has a rough surface where topography defines grain boundaries.

6. The sensor according to claim 1, wherein the semiconducting layer comprises a thin film.

7. The sensor according to claim 6, wherein the thin film comprises a plurality of nanoparticles comprising the beta-molybdenum oxide.

8. The sensor according to claim 7, wherein the nanoparticles are spherical.

9. The sensor according to claim 7, wherein the nanoparticles are non spherical.

10. The sensor according to claim 7, wherein the nanoparticles have homogeneous size.

11. The sensor according to claim 1, further comprising a gate bias between the first and third contacts, wherein the gate bias affects conductivity through the semiconducting layer.

12. The sensor according to claim 11, wherein the gate bias affects energy barriers between grain boundaries.

13. The sensor according to claim 1, wherein the detecting takes place without any thermal requirement.

14. The sensor according to claim 1, wherein the sensor is configured to operate independent of temperature and as a function of gate voltage.

15. The sensor according to claim 1, wherein the sensor is configured to operate at variable conductivity levels.

16. The sensor according to claim 1, wherein the architecture is configured so that the detecting takes place without any thermal requirement.

17. The sensor according to claim 1, further comprising a gate bias between the first and third contacts, wherein the conductivity of the semiconducting layer is greater due to the gate bias.

18. A sensor for detecting the presence of an analyte gas, the sensor comprising:
a substrate;
an insulating layer;
a semiconducting layer separated from the substrate by the insulating layer;
a first contact contacting the semiconducting layer;
a second contact contacting the semiconducting layer; and
a third contact contacting the substrate;
wherein the semiconducting layer consists of beta-molybdenum oxide capable of chemical interaction with the analyte gas, wherein the analyte gas consists of a reducing gas;
wherein the third contact is a conductive layer on the substrate separated from the semiconducting layer by an insulator; and
wherein the insulating layer, the semiconducting layer, first contact, second contact, and third contact are arranged in an architecture predetermined such that the sensor detects a variation in the level of the analyte gas as a variation in a current between the first and second contacts occurring when a voltage is applied across the first contact and the third contact.

* * * * *